(12) United States Patent
Orofino

(10) Patent No.: US 10,441,708 B2
(45) Date of Patent: Oct. 15, 2019

(54) INTERMEDIATE PRODUCT FOR PRODUCING PRE-FILLED DUAL-CHAMBER SYRINGES OR CARTRIDGES AND METHOD OF PRODUCING SAID INTERMEDIATE PRODUCT

(71) Applicant: OROFINO PHARMACEUTICALS GROUP S.r.l., Rome (IT)

(72) Inventor: Ernesto Orofino, Rome (IT)

(73) Assignee: OROFINO PHARMACEUTICALS GROUP S.r.l., Rome (IT)

( * ) Notice: Subject to any disclaimer, the term of this patent is extended or adjusted under 35 U.S.C. 154(b) by 741 days.

(21) Appl. No.: 14/910,187

(22) PCT Filed: Jul. 23, 2014

(86) PCT No.: PCT/IT2014/000193
§ 371 (c)(1),
(2) Date: Feb. 4, 2016

(87) PCT Pub. No.: WO2015/019374
PCT Pub. Date: Feb. 12, 2015

(65) Prior Publication Data
US 2016/0166760 A1 Jun. 16, 2016

(30) Foreign Application Priority Data
Aug. 5, 2013 (IT) .............................. RM2013A0457

(51) Int. Cl.
*A61M 5/00* (2006.01)
*A61J 1/20* (2006.01)
(Continued)

(52) U.S. Cl.
CPC .............. *A61M 5/002* (2013.01); *A61J 1/062* (2013.01); *A61J 1/2093* (2013.01); *A61J 1/2096* (2013.01);
(Continued)

(58) Field of Classification Search
CPC .. A61J 1/06; A61J 1/062; A61J 1/2093; A61J 1/2096; A61M 2207/00; A61M 2209/045;
(Continued)

(56) References Cited

U.S. PATENT DOCUMENTS 6,164,044 A * 12/2000 Porfano ................. B65B 55/10
422/28
2003/0100866 A1 * 5/2003 Reynolds ................ A61J 1/062
604/187

(Continued)

FOREIGN PATENT DOCUMENTS

EP 2 452 708 A1 5/2012
WO 99/15215 A1 4/1999

OTHER PUBLICATIONS

International Search Report for corresponding International Patent Application No. PCT/IT2014/000193 dated Jan. 22, 2015.

*Primary Examiner* — Adam Marcetich
(74) *Attorney, Agent, or Firm* — Merchant & Gould P.C.

(57) ABSTRACT

An intermediate product (1) for producing a plurality of pre-filled dual-chamber syringes or cartridges includes a support template (2) having an array of support seats and partially pre-filled tubular containment bodies (3), each inserted in a respective support seat. Each of the tubular containment bodies (3) 10 extends between a first (4) and a second opening (5). A sterile package (20-23) encloses the support template (2) and the tubular containment bodies (3) in sterile manner. The interiors of the tubular containment bodies (3) include a first stopper (6) and a second stopper (7) arranged in such a manner as to define therebetween a first containment chamber (8) in the tubular containment body (3) and adapted to slide inside the tubular containment 20 body. A liquid substance is contained inside the first containment chamber (8).

10 Claims, 6 Drawing Sheets

(51) Int. Cl.
  *B65B 3/00* (2006.01)
  *B65B 5/06* (2006.01)
  *A61J 1/06* (2006.01)

(52) U.S. Cl.
  CPC .............. *A61M 5/008* (2013.01); *B65B 3/003* (2013.01); *B65B 5/068* (2013.01); *A61M 2207/00* (2013.01); *A61M 2209/045* (2013.01); *B65B 2220/14* (2013.01); *B65B 2220/16* (2013.01); *B65B 2230/02* (2013.01)

(58) Field of Classification Search
  CPC .. A61M 5/002; A61M 5/008; A61M 2209/06; B65B 2220/14; B65B 2220/16; B65B 2230/02; B65B 3/003; B65B 5/068
  See application file for complete search history.

(56) References Cited

U.S. PATENT DOCUMENTS

| | | | |
|---|---|---|---|
| 2004/0138611 A1* | 7/2004 | Griffiths | A61M 5/2033 604/82 |
| 2005/0223677 A1* | 10/2005 | Py | B65B 3/003 53/140 |
| 2007/0060877 A1* | 3/2007 | Bassarab | A61M 5/2448 604/89 |
| 2007/0151882 A1* | 7/2007 | Cocheteux | A61M 5/008 206/366 |
| 2007/0157564 A1* | 7/2007 | Vander Bush | A61M 5/002 53/434 |
| 2008/0230961 A1* | 9/2008 | Moesli | B29C 51/10 264/524 |
| 2009/0288977 A1 | 11/2009 | Vanderbush et al. | |
| 2011/0094189 A1* | 4/2011 | Bottger | B65B 3/003 53/425 |
| 2013/0180999 A1* | 7/2013 | Denning | A61J 1/14 220/625 |
| 2014/0158700 A1* | 6/2014 | Glocker | A61M 5/002 220/737 |
| 2015/0013276 A1* | 1/2015 | Okajima | A61L 2/07 53/471 |
| 2015/0078961 A1* | 3/2015 | Opie | A61L 2/26 422/28 |

* cited by examiner

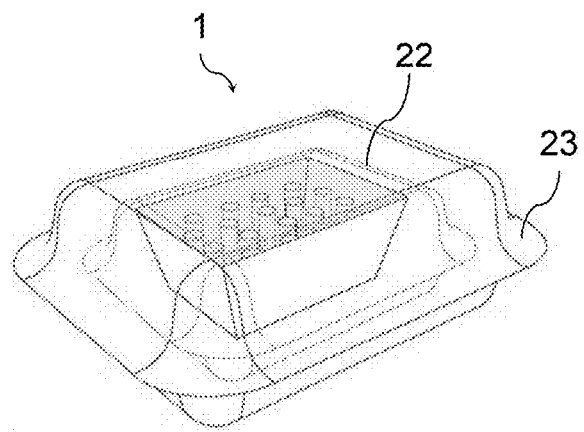
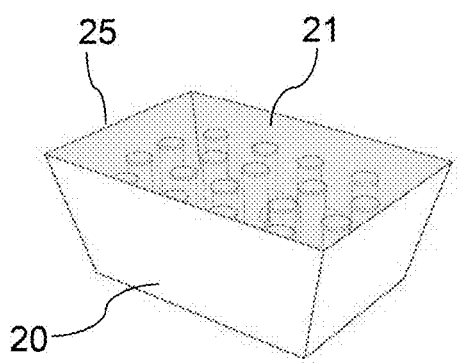
FIG. 1
FIG. 2
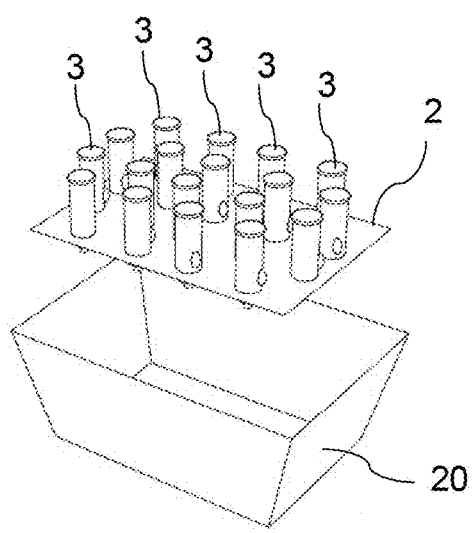
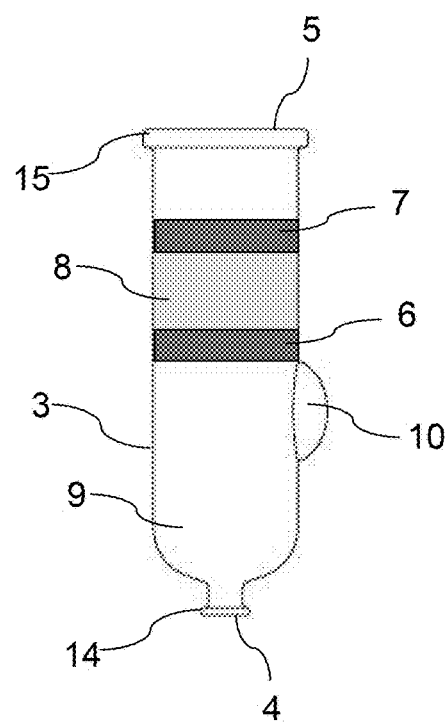
FIG. 3
FIG. 4

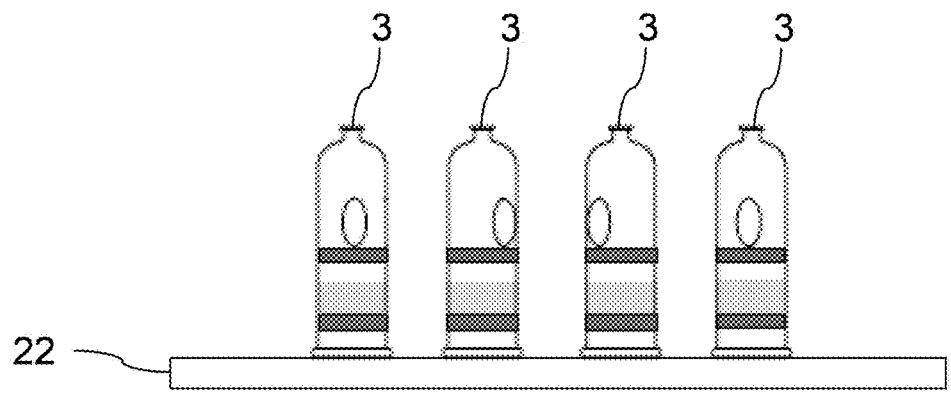
FIG. 12
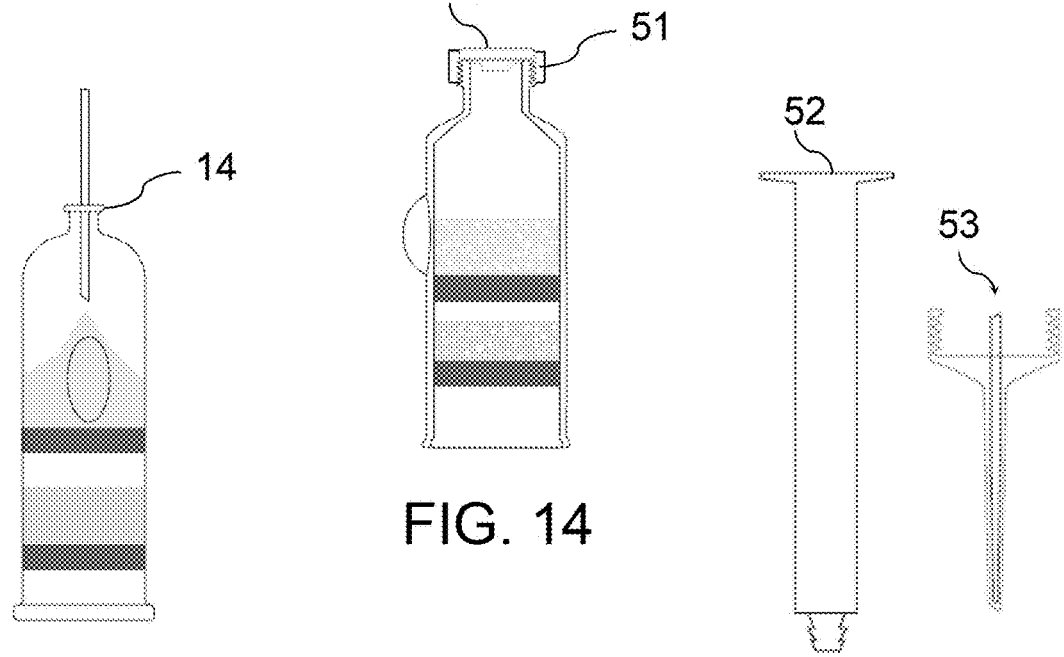
FIG. 13
FIG. 14
FIG. 15

INTERMEDIATE PRODUCT FOR PRODUCING PRE-FILLED DUAL-CHAMBER SYRINGES OR CARTRIDGES AND METHOD OF PRODUCING SAID INTERMEDIATE PRODUCT

This application is a National Stage Application of PCT/IT2014/000193, filed 23 Jul. 2014, which claims benefit of Serial No. RM2013A000457, filed 5 Aug. 2013 in Italy and which applications are incorporated herein by reference. To the extent appropriate, a claim of priority is made to each of the above disclosed applications.

BACKGROUND OF THE INVENTION

The present description relates to the technical field of dual-chamber cartridges and syringes and in particular relates to an intermediate product for producing pre-filled dual-chamber syringes or cartridges and method of producing said intermediate product.

Pre-filled dual-chamber syringes or cartridges have been known for a long time and are today widely used. Said dual-chamber syringes or cartridges comprise a tubular containment body and two substances, of which at least one is a liquid substance, contained in two separate chambers defined inside the containment body.

The two substances, which are for example a solid substance and a liquid substance, are intended to be mixed one with the other immediately before injection. The liquid substance is for example a solvent for injectable use. For the mixing of the two substances the two chambers are placed in communication one with the other to reconstitute an injectable solution, for example by providing a bypass element in the pre-filled syringe or cartridge.

WO99/15215 describes, referring to FIG. 4 of this document, a method of filling a dual-chamber syringe shaped like an ampoule, wherein the filling of the two chambers takes place in a sterile chamber 40, in which are provided in sequence:

the insertion of the middle stopper in the syringe (step indicated as "MIDDLE PLUNGER CHARGING");

the charging of the front chamber of the syringe with a solution (step indicated as "SOLUTION CHARGING") on the side of the front opening of the syringe;

lyophilization of the abovementioned solution (step indicated as "LYOPHILIZATION");

closure of the front opening of the syringe (step indicated as "SEALING");

filling with the solvent (step indicated as "SOLVENT CHARGING");

the insertion of the rear stopper in the syringe (step indicated as "REAR PLUNGER CHARGING");

The need is felt to provide a method of filling of a dual-chamber syringe or cartridge which, compared to filling methods of the prior art, is simple and flexible in relation to the type of substances to be dosed inside the chambers of the syringe or cartridge.

A general object of the present description is that of making available an intermediate product for the production of pre-filled syringes or cartridges which allows the abovementioned need to be fulfilled.

SUMMARY OF THE INVENTION

The object of the present description is also a method for the production of the intermediate product and a method of pre-filling of a dual-chamber syringe or cartridge.

BRIEF DESCRIPTION OF THE DRAWINGS

The invention will be made clearer by the following detailed description of its embodiments, given by way of an example and therefore in no way limiting in relation to the accompanying drawings, in which:

FIG. 1 shows an intermediate product for producing a plurality of pre-filled dual-chamber syringes or cartridges;

FIG. 2 shows a support template of the intermediate product of FIG. 1 comprising an array of support seats and a plurality of partially pre-filled tubular containment bodies, each inserted in a respective support seat, in a configuration in which the support template is inserted inside a containment tray;

FIG. 3 shows the support template of FIG. 2 in a condition in which the support template is extracted from the containment tray;

FIG. 4 shows one of the partially pre-filled containment bodies of FIG. 2;

FIG. 12 shows the partially pre-filled containment bodies after one of the steps of the method of FIG. 11;

FIG. 13 shows a step of dosing of the method of FIG. 11;

FIG. 14 shows a part of a pre-filled syringe or cartridge as obtained in output from the method of FIG. 11;

FIG. 15 shows some components which can be associated to the part of syringe or cartridge of FIG. 14.

DETAILED DESCRIPTION OF THE PREFERRED EMBODIMENTS

Figure 5:
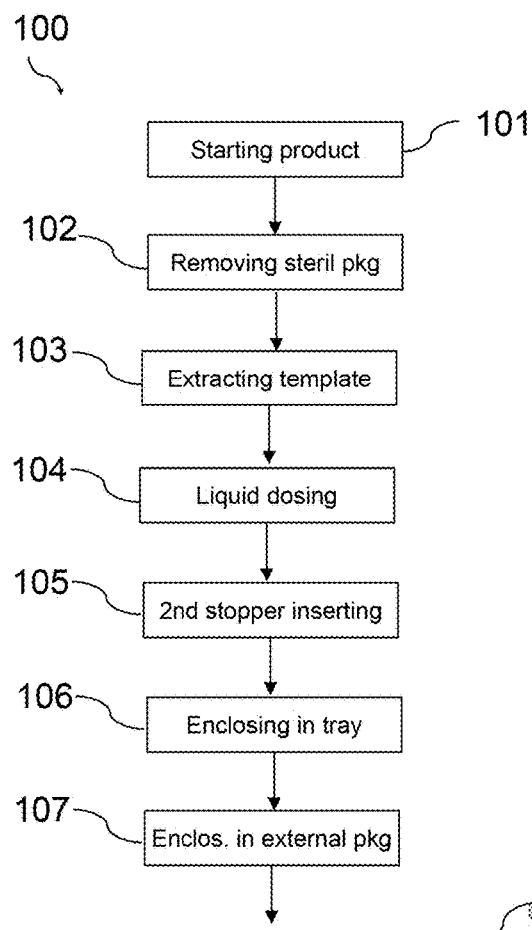
FIG. 5 shows a schematic flow diagram of a method of production of the intermediate product.

In the accompanying drawings identical or similar elements are to be denoted by the same reference numerals.

In the accompanying drawings reference numeral 1 denotes overall a preferred and non-limiting embodiment of intermediate product for the industrial production of a plurality of pre-filled dual-chamber syringes or cartridges.

Referring to FIGS. 1 to 4, the intermediate product 1 comprises:

a support template 2 comprising an array of support seats;

a plurality of partially pre-filled tubular containment bodies 3, each inserted in a respective support seat, each of the tubular containment bodies 3 extending between a first 4 and a second opening 5.

The abovementioned openings 4,5 are preferably free and are axially spaced one from the other along an axis of main extension of the tubular containment body 3. The first opening 4, or front opening 4, preferably has a smaller diameter with respect to the diameter of the second opening 5, or rear opening 5.

At the abovementioned openings 4,5 the tubular containment body 3 preferably has respective collars 14, projecting towards the exterior of the body 3. The collar 14 placed at the first opening 4 is preferably an externally threaded collar.

In accordance with an embodiment the support template 2 has a main body, for example plate-shaped, comprising a plurality of support openings inside of which the containment bodies 3 are inserted. These support openings support the containment bodies 3 for example through interference of their rims against the outer walls of the bodies 3. The support template 2 is preferably made in plastic material.

The tubular bodies 3 are for example in the form of the containment bodies of a syringe or of a cartridge suitable for containing injectable substances and are for example made in glass or in a transparent or substantially transparent plastic material. The tubular bodies 3 are preferably each made in a single piece.

The intermediate product 1 also comprises a sterile package 20-23 inside which the support template 2 and the plurality of tubular containment bodies 3 are enclosed in a sterile manner. For example this sterile package 20-23 is a package produced aseptically.

The tubular containment bodies 3 comprise in the interior thereof:

a first 6 and a second stopper 7 arranged in such a manner as to define therebetween in the tubular containment body 3 a first containment chamber 8, or rear chamber 8, and suitable for sliding inside the tubular containment body (for example due to a thrust or traction force);

a first liquid substance contained inside the first containment chamber 8.

The abovementioned first liquid substance is preferably a solvent for injectable use, for example a WFI (water for injection) solvent or a solution of lidocaine or a solution of water and benzyl alcohol or a physiological solution of sodium chloride or in general any injectable substance suitable for reconstituting another solid or liquid substance. The first liquid substance can be or contain an API (active pharmaceutical ingredient).

The stoppers 6,7 are made for example in plastic material, are such as to seal-engage with the internal walls of the tubular body 3 and are such as to be able to slide inside the tubular body 3 under the action of a thrust or traction force.

The first stopper 6, or middle stopper 6, is spaced from the first opening 4 in such a manner as to define between the first stopper 6 and the first opening a second containment chamber 9, or rear chamber 9, empty and suitable for being filled with a second substance, solid or liquid, intended to be mixed inside the containment body with said first liquid substance in order to reconstitute an injectable solution. In the case wherein the second substance is solid, it can be crystallized or lyophilized. The version in which the second substance is crystallized and not lyophilized is currently preferred. The second substance is preferably a powder, a substance in granules or a sterile tablet. The abovementioned second substance can be or contain an API. In accordance with an embodiment, the abovementioned second substance comprises two separate substances for example in the form of two separate tablets, each one containing one of said two separate substances.

The aforesaid second substance is for example a highly active substance, such as for example: a beta-lactam antibiotic or a cytotoxic antitumor agent or a hormone or a biological preparation. The abovementioned second substance can also be a normal active ingredient, i.e. which cannot be defined as a highly active ingredient.

In accordance with an embodiment the first stopper 6, or middle stopper 6, comprises at least one bypass channel permanent in a state of closure and adapted for being brought into a state of opening following the stress of an external force, for example a force of pressure acting on the stopper. The stoppers with bypass channels are generally known to a person skilled in the art of dual-chamber injection devices and for this reason will not be described further.

In accordance with an alternative embodiment the containment body 3 comprises an internal wall provided with a recess 10 adapted to define a bypass channel. This recess is positioned between the first stopper 6 and the first opening 4.

Preferably the second stopper 7, or rear stopper 7, comprises a fastening element adapted to fasten a plunger to the second stopper 7 in such a manner that the second stopper 7 can slide inside the containment body 3 under the action of the plunger. Said fastening element comprises for example an internally threaded blind hole formed in the thickness of the second stopper 7, inside whereof a complementary threaded end portion of the plunger can be inserted and screwed.

In accordance with an embodiment the sterile package 20-23 comprises a containment tray 20, and the support template 2 is accommodated and closed in a sterile manner, together with the tubular containers 3, inside the containment tray 20, for example in a position in which the support template is spaced and parallel to a bottom wall of the containment tray 20. The containment tray 20 is preferably a tray in plastic material.

In accordance with an embodiment the containment tray 20 comprises an opening rim 25 and the package 20-23 comprises a closure film 21, for example a film in plastic material, fastened flush to said rim 25 and resting on an end portion of the tubular containment bodies 3. For example this film is heat welded to the opening rim 25.

The package 20-23 preferably comprises a first sterile pouch 22 which contains the containment tray 20. This sterile pouch 22 is for example made in a flexible multilayer laminate. The package 20-23 preferably comprises a second sterile pouch 23 which encloses the first sterile pouch 22. This sterile pouch 22 is for example also made in a flexible multilayer laminate.

Referring to FIG. 5 a description will now be given of a production method 100 for an intermediate product 1, of the type described above, for producing a plurality of pre-filled dual-chamber syringes or cartridges.

Figure 6:
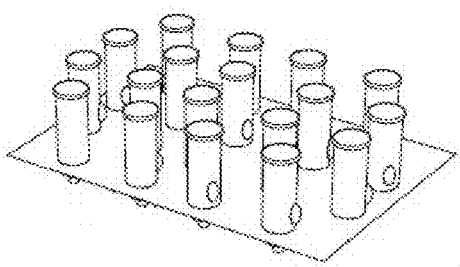
FIG. 6 shows a possible starting product of the method of FIG. 5.
Figure 7:
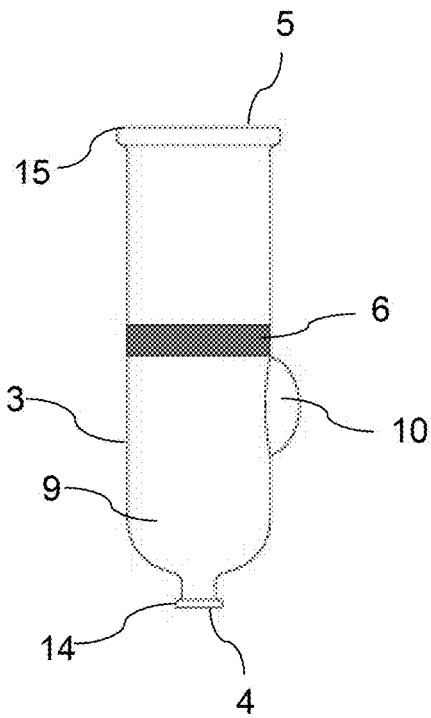
FIG. 7 shows a tubular container of the starting product of FIG. 6.

The method 100 comprises a step 101 of providing a starting product comprising a support template 2 comprising an array of support seats. The starting product comprises a plurality of tubular containment bodies 3, each inserted in a respective support seat. The abovementioned starting product takes shape in the assembly 2,3 shown in FIG. 6 in which the containment bodies are presented as shown in FIG. 7, in which it can be noted that there is only one stopper inserted inside the tubular body 3. Referring to FIG. 7, the containment bodies 3 of the starting product 2,3 differ from the containment bodies 3 of the intermediate product 1 already described with reference to FIG. 4 due only to the fact that in this case the second stopper 7 and the solvent 8 are not provided. For economy of disclosure the containment bodies 3 of the intermediate product will not be described here in greater detail.

Figure 8:
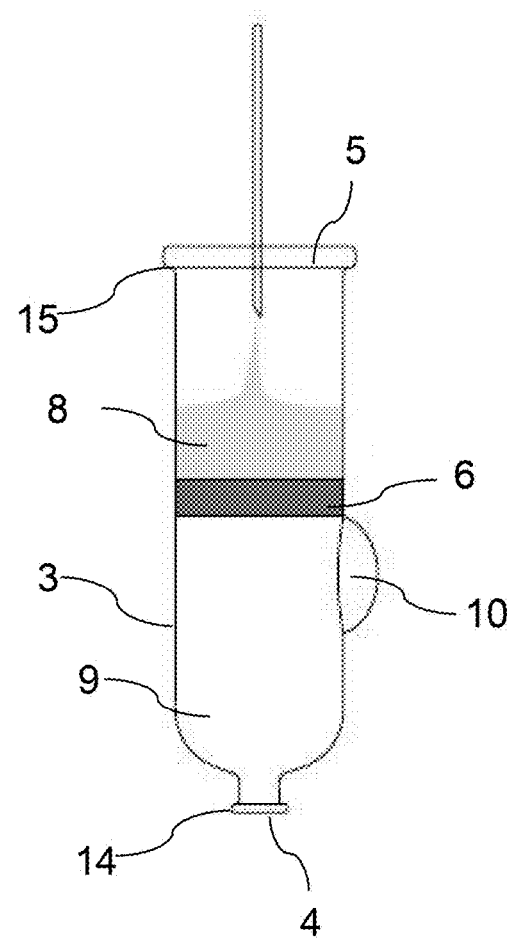
FIG. 8 shows a step of dosing of the solvent of the method of FIG. 5.

The method 100 comprises a step of dosing 104 of the first liquid substance, or solvent 8, through the second opening 5. The dosing step 104 is schematically illustrated in FIG. 8. The dosing step 104 can be performed simultaneously for more than one or for all the containment bodies 3 of the plurality of containment bodies 3 of the starting product.

The method 100 comprises a step 105 of inserting a second stopper 7, or rear stopper 7, through the second opening 5 in order to define a first containment chamber of the abovementioned first liquid substance between the first stopper 6 and the second stopper 7. In this way a configuration of the containment body 3 is obtained as already represented in FIG. 4 and already described previously. Between the dosing step 104 and the step 105 of inserting the second stopper 7 no step of lyophilization of the first substance is provided.

The method 100 comprises a step of enclosing 106 the support template 2 and the plurality of tubular containment bodies 3 inside a sterile package 20-23, for example produced aseptically. This step 106 is for example such as to lead to the production of an intermediate product as shown in FIG. 1.

In particular, in accordance with an embodiment, the sterile package 20-23 comprises a containment tray 20, and the step of enclosing 106 the support template 2 comprises a step of inserting the template 2 inside the containment tray 20 and of closing the containment tray in a sterile manner. The containment tray 20 preferably comprises an opening rim 25 and the step of closing the containment tray 20 in a sterile manner comprises a step of fastening a closure film 21 flush with the rim 25. More preferably the enclosing step 106 comprises a step of enclosing the containment tray 20 inside the sterile pouch 22. It may also be foreseen that the enclosing step 106 comprises a step of enclosing the first sterile pouch 22 in a second sterile pouch 23 to arrive at the configuration of the intermediate product as shown in FIGS. 1-4.

Figure 9:
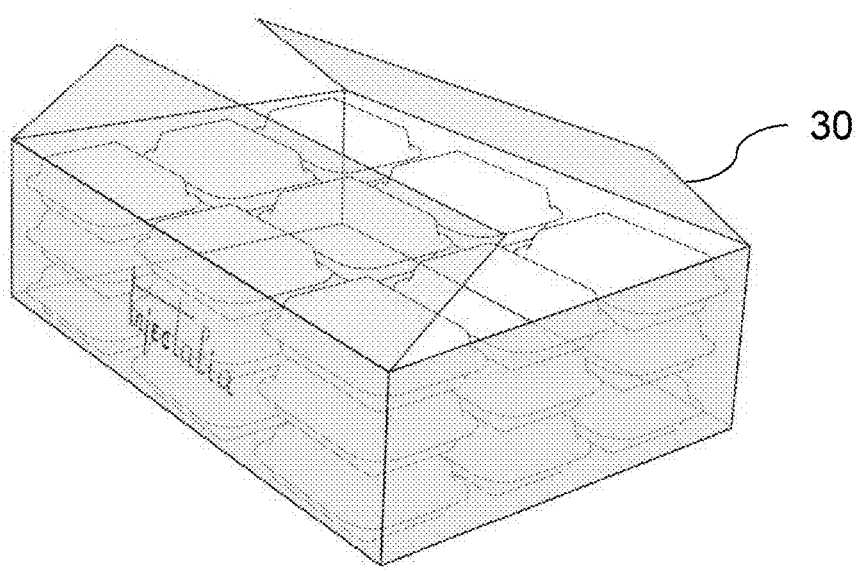
FIG. 9 shows a plurality of intermediate products inserted inside an external package.

Referring to FIG. 9, in accordance with an embodiment, a further step 107 can be provided of inserting and closing several intermediate products 1 inside an external package 30.

In the case wherein the abovementioned starting product also comprises a sterile package 20-23 comprising the abovementioned containment tray 20 and in the case wherein the support template 2 is contained in the containment tray 20 in the starting product, the method 100 can comprise, before the dosing step 104, a step of removing 102 the sterile package 20-23 and a step of extracting 103 the support template 2 from the containment tray 20.

Figure 10:
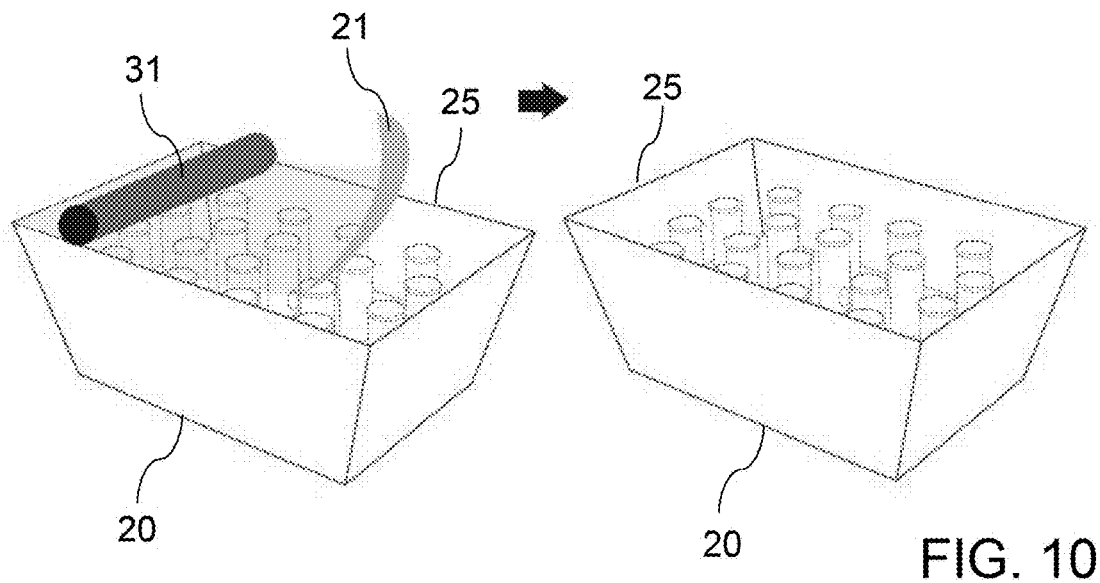
FIG. 10 shows another step of the method of FIG. 5.

Referring to FIG. 10, in the case wherein also in the abovementioned starting product the containment tray 20 comprises an opening rim 25 whereto a closure film 21 is fastened flush, the step of removing 102 the sterile package 20-23 comprises a step of removing the closure film 21. For example the closure film 21 can be removed by means of a hot roller 31.

In the case wherein also in the starting product the sterile package 20-23 comprises one or more sterile pouches 22-23, the removing step 102 provides a step of removing said one or more sterile pouches 22, 23 performed before the removal of the closure film 21.

The abovementioned steps 103 to 106 of the method 100 can all be performed in a first sterile chamber, for example in a sterile chamber of a liquids dosing machine, in which in fact the first liquid substance or solvent is dosed. As far as step 102 is concerned, the pouches 22-23, if provided, are preferably removed outside of the first sterile chamber while the closure film 21, if provided, is preferably removed inside the first sterile chamber. Moreover the phase of closing 107 in a further package 30 is performed outside of the first sterile chamber.

The intermediate products as provided in output from steps 106 or 107 can be transported in input to a second sterile chamber separate from the first sterile chamber for performing a method of production of a pre-filled dual-chamber syringe or cartridge. For example and without thereby introducing any limitation, the abovementioned intermediate products can be transported as far as the entrance of the sterile chamber (referred to here as second sterile chamber) of a machine for dosing highly contaminating substances, for example a dosing machine of antibiotic powders. The second sterile chamber can be located in the same production plant in which the first sterile chamber is located or in another geographically distant production plant.

Figure 11:
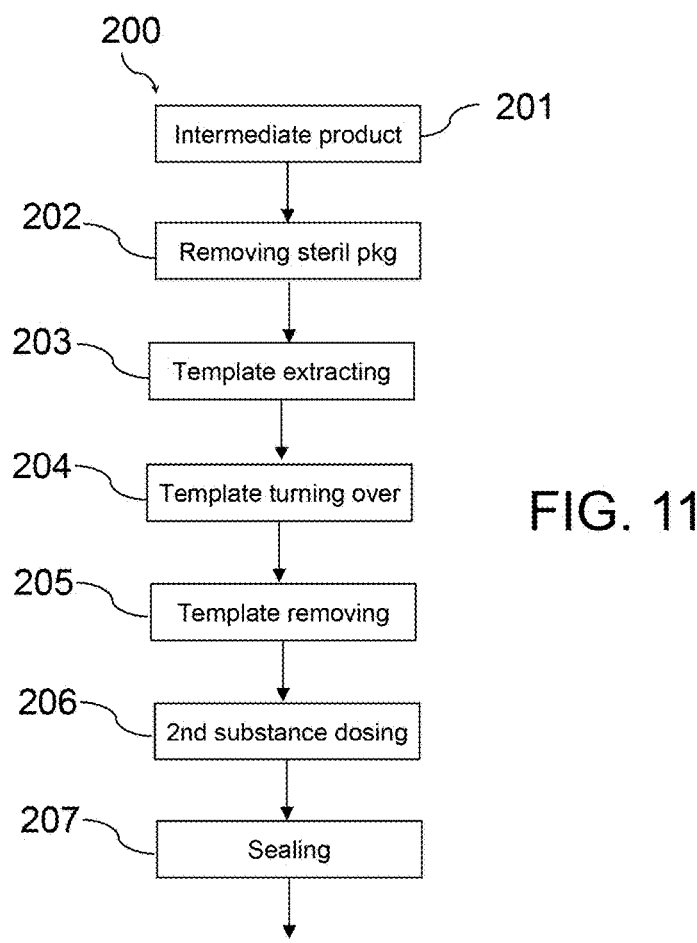
FIG. 11 shows a schematic flow diagram of a method of filling of a dual-chamber syringe or cartridge.

An embodiment of the abovementioned method 200 of production of a pre-filled dual-chamber syringe or cartridge is schematically shown in the flow diagram of FIG. 11.

The method of filling 200 of a dual-chamber syringe or cartridge comprises a step of providing 201, for example at the entrance of the second sterile chamber described above, an intermediate product 1 as described with reference to FIGS. 1-4 in any one of its possible variants and embodiments described and in particular in an orientation of the intermediate product in which the containment bodies 3 have the second opening 5 which is located above the first opening 4.

The filling method 200 comprises:

a step 202 of removing the sterile package 20-23;

a step 204 of turning over the support template 2 such that the first opening 4 is located above the second opening 5;

a step of dosing 206 through the first opening 4 the second substance, solid or liquid, intended to be mixed inside the containment body 3 with first liquid substance in order to reconstitute an injectable solution;

a step of sealing 207 the first opening 4.

The dosing step 206 for example includes the dosing of a powder or of one or more tablets. In the latter case the second substance can comprise more than one substance and the dosing is provided of one tablet for each substance.

In accordance with a preferred embodiment, between the dosing step 206 and the sealing step 207 the lyophilization of the second substance is not provided.

In accordance with an embodiment in which the abovementioned sterile package 20-23 comprises a containment tray 20 which accommodates the support template 2, the method comprises, before the dosing step 206, a step of taking 203 the support template 2 out of the containment tray 20 (as shown in FIG. 3). Referring to FIG. 12, in the method 200 after the step of turning over the support template 2 and before the dosing step 206 a step of removing 205 the support template 2 is moreover preferably provided, leaving the tubular bodies on a surface or device of resting and/or support provided in the dosing machine.

The abovementioned steps 203 to 206 are performed inside the second sterile chamber. The phase of removing 202 the sterile package can be performed partly outside the second sterile chamber and partly inside the second sterile chamber. In particular, in the case wherein the containment tray 20 has an opening rim 25 closed by a closure means 21 fastened flush to the opening rim 25, the step of removing 202 the sterile package 20-23 comprises a step of removing the closure means 21, preferably performed inside the second sterile chamber.

In the case wherein the sterile package 20-23 comprises at least one sterile pouch 22,23 containing the containment tray 20 and the support template 2, the step of removing 202 the sterile package 20-23 comprises a step of opening and removing said at least one sterile pouch 22,23, preferably performed outside of the second sterile chamber and before removal of the closure means 21.

Referring to FIG. 14, the step of sealing 207 the first opening 4 comprises a step of attaching a closure means 50 to the first opening 4 and fastening a crimp closure 51 to the containment body in the vicinity of the first opening 4 to lock the closure means to the tubular body 3.

The abovementioned step of sealing 207 the first opening 4 is preferably performed inside the second sterile chamber. Said crimp closure 51 can be such as to engage with the collar 14 of the containment body 3.

After the step of sealing 207 the step can be provided of packaging the product obtained in this way with a plunger 52, intended to be attached to the second stopper 7, and a needle 53 provided with an attachment flange for example threaded internally, for the fastening to the tubular body 3 once the crimp closure 51 has been removed. A packaged kit of parts is thus obtained which, assembled one with the other, form a pre-filled dual-chamber injection device as for example shown in FIG. 16.

During operation, the pressure of the plunger determines the sliding of the two stoppers 6,7 inside the tubular body 3. In the case wherein the bypass channel 10 is provided, when the first stopper 6 is located at the channel 10, the containment chambers come into communication one with the other and the first liquid substance penetrates the second chamber, mixing with the second substance contained therein to reconstitute an injectable solution.

On the basis of what is described above it is therefore possible to understand that the intermediate product 1 and the processes proposed allow full achievement of the objects mentioned above with reference to the prior art.

Figure 16:
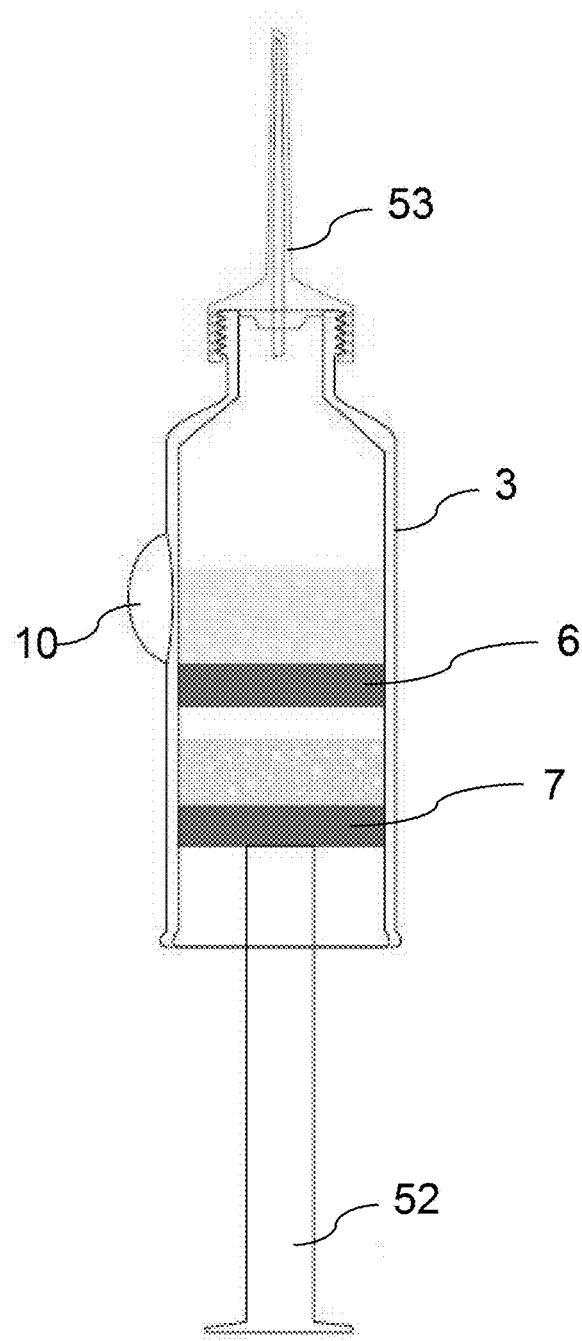
FIG. 16 shows a syringe or cartridge obtained by attaching one to the other the part shown in FIG. 14 and the components shown in FIG. 15.

Referring to FIG. 16, it is noted that in the present description a pre-filled dual-chamber syringe or cartridge was also described, comprising:

a tubular containment body 3 made in a single piece which extends between a first 4 and a second opening 5;

a first 6 and a second stopper 7 arranged in such a manner as to define therebetween in the tubular containment body 3 a first containment chamber 8;

a first liquid substance contained inside the first containment chamber 8;

a closure means removably attached to the first opening 4; in which the first stopper 6 is spaced from the first opening 4 in such a manner as to define between the first stopper 6 and the first opening 4 and inside said tubular body a second containment chamber 9 filled with a second highly active substance adapted to be mixed inside the containment body with said first liquid substance in order to reconstitute an injectable solution. For example, the aforesaid second highly active substance is a beta-lactam antibiotic or a cytotoxic antitumor agent or a hormone or a biological preparation.

Without prejudice to the principle of the invention, its embodiments and its details of manufacture may be widely varied with respect to what has been described and illustrated purely by way of a non-limiting example, without thereby departing from the scope of protection as defined in the annexed claims.

The invention claimed is:

1. An intermediate product for producing a plurality of pre-filled dual-chamber syringes or cartridges, comprising:
    a support template comprising an array of support seats;
    a plurality of partially pre-filled tubular containment bodies, each of the tubular containment bodies being inserted in a respective support seat, each of the tubular containment bodies extending between a first opening and a second opening;
    a sterile package inside which the support template and the plurality of tubular containment bodies are enclosed in sterile manner; the sterile package comprising:
    a containment tray, the support template being accommodated inside the containment tray, the containment tray comprising an opening rim in which the sterile package comprises a closure film fastened flush to said rim and resting on an end portion of said tubular containment bodies:
    a first sterile pouch containing the containment tray;
    wherein the tubular containment bodies comprise in the interior thereof:
    a first stopper and a second stopper arranged to define therebetween in the tubular containment body a first containment chamber and adapted to slide inside the tubular containment body;
    a first liquid substance contained inside the first containment chamber;
    wherein the first stopper is spaced from the first opening to define between the first stopper and the first opening a second containment chamber, the second containment chamber being empty and adapted to be filled with a second substance to be mixed inside the containment body with said first liquid substance in order to reconstitute an injectable solution.

2. An intermediate product according to claim 1, wherein: the first stopper comprises at least one bypass channel; or the containment body comprises an internal wall equipped with a recess adapted to define a bypass channel, and the recess is located between the first stopper and the first opening.

3. An intermediate product according to claim 1, wherein the tubular containment body is made in a single piece.

4. An intermediate product according to claim 1, wherein the second stopper comprises a fastening element adapted to fasten a plunger to the second stopper such that the second stopper can slide inside the containment body under action of the plunger.

5. An intermediate product according to claim 1, wherein the package comprises a second sterile pouch which encloses the first sterile pouch.

6. A production method for an intermediate product for producing a plurality of pre-filled dual-chamber syringes or cartridges, comprising in sequence the steps of:
    providing a starting product comprising a support template comprising an array of support seats, the starting product comprising a plurality of tubular containment bodies each of the tubular containment bodies being inserted in a respective support seat, each of the tubular containment bodies extending along a vertical axis between a first opening and a second opening, the containment bodies comprising a first stopper inserted inside the containment body between the first opening and the second opening, the second opening being located at a higher level relative to the first opening;
    dosing a first liquid substance through the second opening;
    inserting a second stopper through the second opening to define a first containment chamber of the first liquid substance between the first stopper and the second stopper;
    enclosing the support template and said plurality of tubular containment bodies inside a sterile package;
    wherein the sterile package comprises a containment tray, and wherein the step of enclosing the support template comprises a step of inserting the template inside the containment tray and of closing the containment tray; and wherein the containment tray comprises an opening rim and wherein the step of closing said containment tray comprises a step of fastening a closure film flush with the rim.

7. A production method according to claim 6, wherein the enclosing step comprises a step of enclosing the containment tray inside a sterile pouch.

8. A production method according to claim 7, wherein the enclosing step comprises a step of enclosing the first sterile pouch in a second sterile pouch.

9. A production method according to claim 6, wherein the starting product comprises said containment tray, wherein the support template is contained in the containment tray in the starting product, and wherein the method comprises, before the dosing step, a step of extracting the support template from the containment tray.

10. A production method according to claim 6, wherein between the dosing step and the inserting step, the method is free of a lyophilization step.

* * * * *

UNITED STATES PATENT AND TRADEMARK OFFICE
CERTIFICATE OF CORRECTION

PATENT NO. : 10,441,708 B2  
APPLICATION NO. : 14/910187  
DATED : October 15, 2019  
INVENTOR(S) : Ernesto Orofino Page 1 of 1

It is certified that error appears in the above-identified patent and that said Letters Patent is hereby corrected as shown below:

On the Title Page

Item [30], "Aug. 5, 2013 (IT) RM2013A0457" should read -- Aug. 5, 2013 (IT) RM2013A000457 --

Signed and Sealed this  
Twenty-fourth Day of December, 2019

Andrei Iancu  
*Director of the United States Patent and Trademark Office*